US00PP31050P2

(12) United States Plant Patent
Van Swieten

(10) Patent No.: US PP31,050 P2
(45) Date of Patent: Nov. 12, 2019

(54) ***PHALAENOPSIS* ORCHID PLANT NAMED 'PHALGORYQ'**

(50) Latin Name: ***Phalaenopsis* hybrid**
Varietal Denomination: PHALGORYQ

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/350,622

(22) Filed: Dec. 11, 2018

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ..... A01H 5/02; A01H 6/62
See application file for complete search history.

(56) References Cited

PUBLICATIONS

PLUTO Plant Variety Database Jul. 13, 2019. p. 1.*

* cited by examiner

*Primary Examiner* — Annette H Para
(74) *Attorney, Agent, or Firm* — Jondle & Associates, P.C.

(57) ABSTRACT

A new and distinct variety of *Phalaenopsis* plant named 'PHALGORYQ', particularly characterized by having very light purple flowers with light reddish-purple shade and very light purple lips, 1 to 3 peduncles that are long and sturdy, leaves that are obovate, and is propagated by meristern tissue culture, is disclosed.

3 Drawing Sheets

Genus and species: *Phalaenopsis* hybrid.
Variety denomination: 'PHALGORYQ'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGORYQ'.

The new *Phalaenopsis* plant is a product of a planned breeding program conducted by the inventor in Bleiswijk, The Netherlands. The objective of this breeding program was to create a new *Phalaenopsis* plant with numerous attractive very light purple flowers with light reddish-purple shade and very light purple lips, suitable for potted plant production.

The new *Phalaenopsis* plant 'PHALGORYQ' is a result of cross-pollination made by the inventor in March 2008 in Bleiswijk, The Netherlands, of the proprietary female, or seed parent, *Phalaenopsis* hybrid '01-2036' (unpatented) with the proprietary male, or pollen parent, *Phalaenopsis* hybrid '01-1988' (unpatented).

The new *Phalaenopsis* was selected by the inventor as a single plant within the progeny of the stated cross-pollination in a controlled greenhouse in Bleiswijk, The Netherlands, in December 2011. Asexual reproduction of the new *Phalaenopsis* plant by meristem tissue culture since 2014 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 24, 2017. 'PHALGORYQ' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands, and can be used to distinguish 'PHALGORYQ' as a new and distinct variety of *Phalaenopsis* plant:

1) Very light purple flowers with light reddish-purple shade and very light purple lips;
2) 1 to 3 peduncles;
3). Peduncle is long and sturdy; and
4) Shape of the leaf is obovate.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week old plants in November 2018. Colors in the photographs may differ from the color values cited in the detailed botanical description, which accurately describe the actual colors of the new variety.

DESCRIPTION OF THE NEW VARIETY

Figure 1:
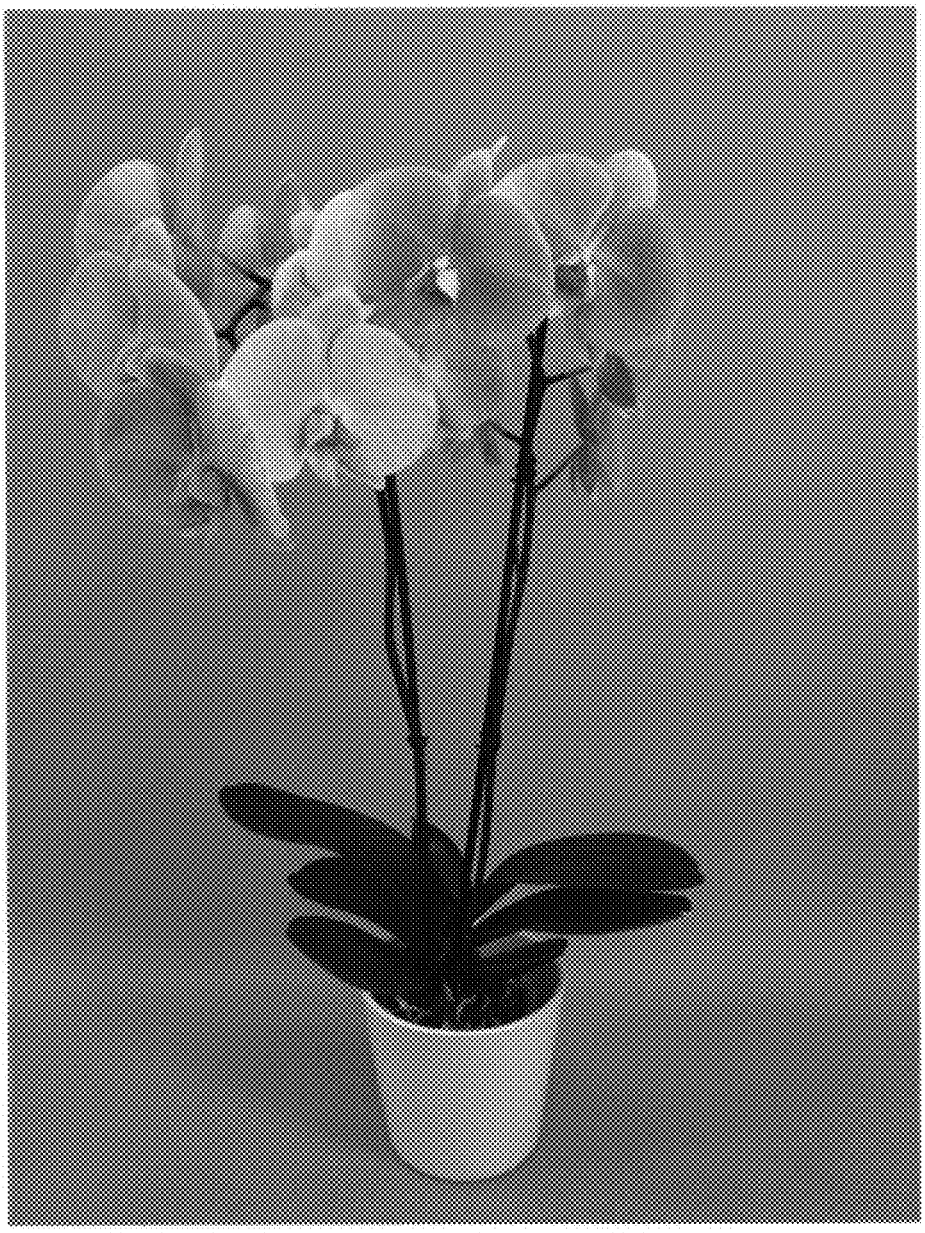
FIG. 1 shows the overall plant habit, including blooms and foliage of 'PHALGORYQ'.
Figure 2:
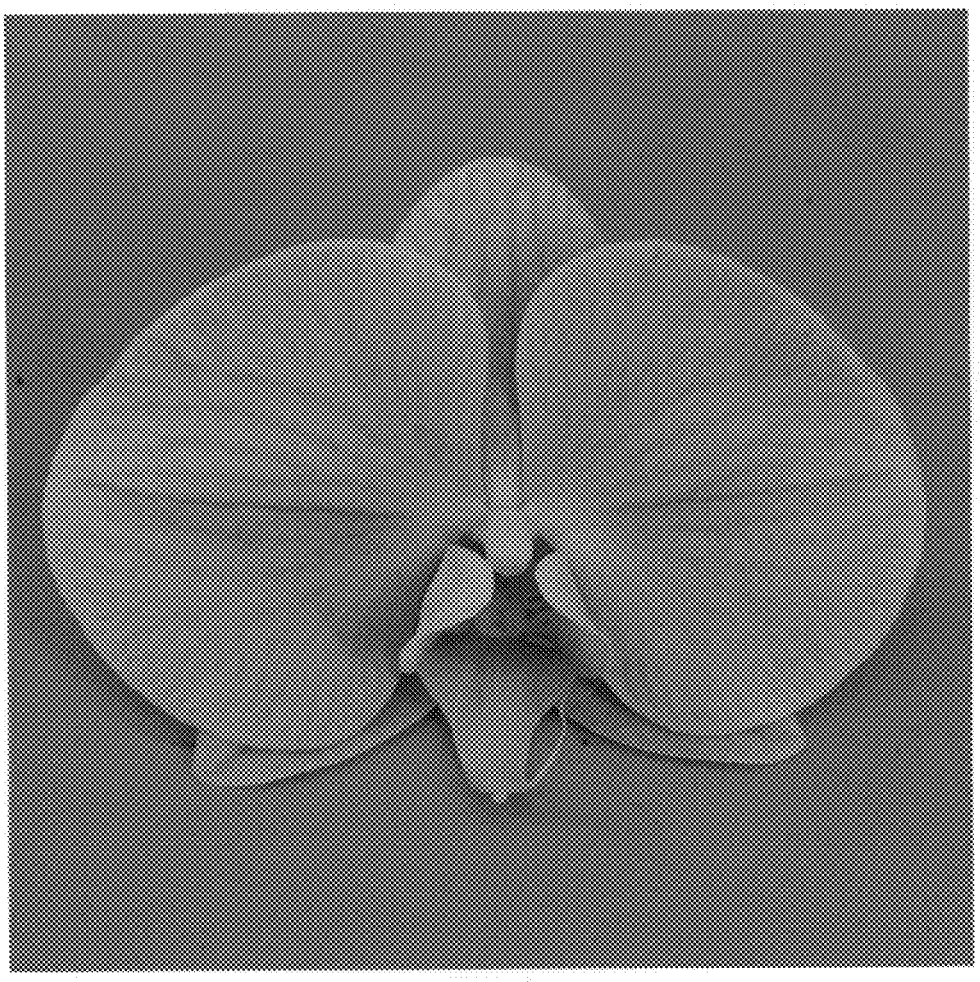
FIG. 2 shows a close-up of a flower of 'PHALGORYQ'.
Figure 3:
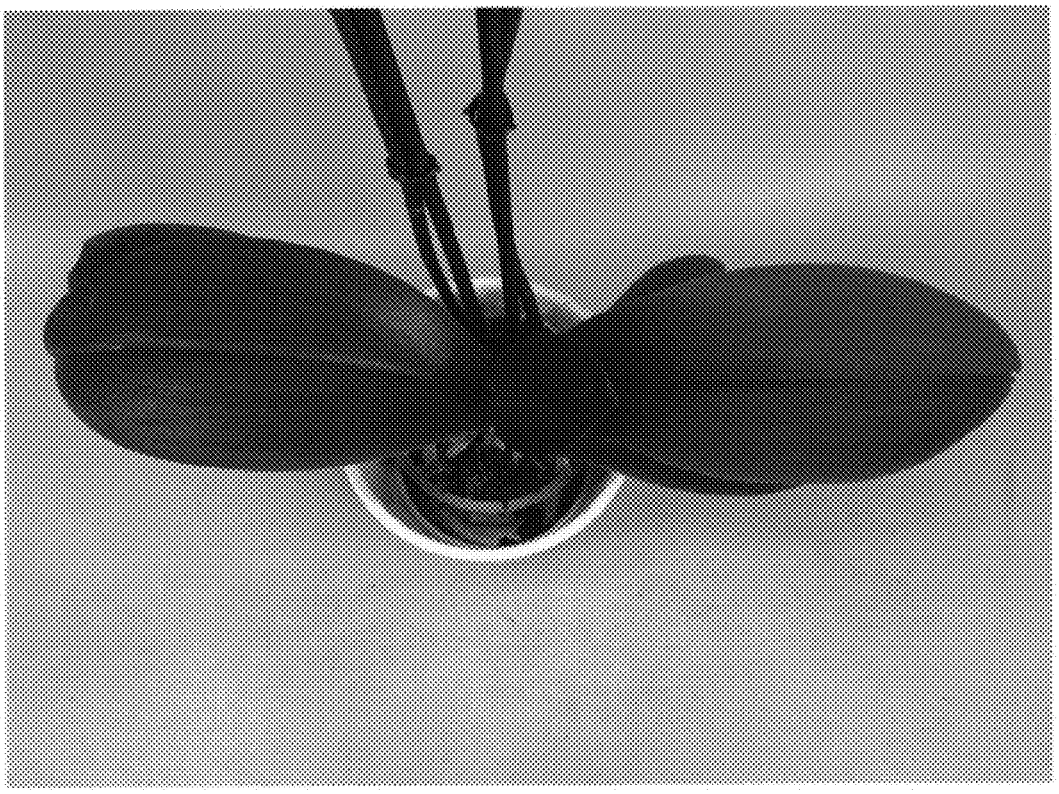
FIG. 3 shows an overhead view of the leaves of 'PHALGORYQ'.

The following detailed description sets forth the distinctive characteristics of 'PHALGORYQ'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in November 2018 on flowering plants which were planted in 12 centimeter (diameter) pots. After in-vitro propagation, the plants were grown in nursery trays for 20-24 weeks, followed by transplantation to 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12 centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGORYQ'.

Parentage:

*Female parent*.—*Phalaenopsis* cultivar '01-2036' (unpatented).

*Male parent*.—*Phalaenopsis* cultivar '01-1988' (unpatented).

Propagation:

*Type*.—Meristem tissue culture.

Roots:

*Root description*.—Greyed-green (RHS 190B/C) colored roots with branching lateral roots having dark red and green (RHS 187C and 146D) colored root tips.

Plant:

*Commercial crop time to flowering*.—Following asexual propagation (in-vitro), the rooted cuttings grow for 20-24 weeks. After transplantation into 12 cm pots, the plants are finished after 48 to 50 weeks.

*Growth habit of peduncle*.—Upright to slightly pendant with raceme to panicle inflorescence.

*Height (from soil level to top of inflorescence)*.—Approximately 59.0 cm to 64.0 cm.

*Width (measured from leaf tips)*.—About 37.0 cm to 39.0 cm.

*Vigor*.—Moderate.

Leaves:

*Mature leaves*.—Quantity per plant: 7 to 9 leaves are produced before flowering. Length (fully expanded): 19.0 cm to 21.0 cm. Width: 9.0 cm to 10.0 cm. Shape: Obovate. Base shape: Moderately elongated. Apex: Obtuse to rounded unequal. Leaf blade angle with the petiole (measured from the horizontal position): Between 30 degrees and 40 degrees. Leaf margin: Entire. Color: Upper surface: RHS 147A. Lower surface: RHS 146A. Texture (upper surface): Rough. Thickness: 2.0 mm to 2.4 mm. Venation: Pattern: Parallel. Color of the midvein: Upper surface: RHS 147A. Lower surface: RHS 146A.

Peduncle:

*Quantity per plant*.—1 to 3.

*Number of flowers per peduncle*.—8 to 12.

*Length*.—59.0 cm to 64.0 cm.

*Diameter*.—5.9 mm to 6.4 mm.

*Strength*.—Strong.

*Aspect*.—Upright to slightly pendant.

*Texture*.—Smooth.

*Color*.—Mix of brown (RHS N200A) and green (RHS 147C).

*Internode length*.—4.5 cm to 5.5 cm.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 220.0 mm to 260.0 mm.

*Flowering time*.—First flowers can be expected 10 to 11 months after planting in a 12 cm (diameter) pot.

*Flower*.—Height: 87.0 mm to 92.0 mm. Diameter: 115.0 mm to 120.0 mm. Depth of lip: 25.0 mm to 27 0 mm.

*Flower longevity*.—On the plant: 12 to 17 weeks.

*Fragrance*.—Absent.

*Flower bud*.—Average size: Large. Length: 27.0 mm to 29.0 mm. Width: 22.0 mm to 24.0 mm. Shape: Egg shaped. Color: Purplish-red (RHS N77B).

*Petals*.—Arrangement: Open/free. Shape: Semi-circular. Apex: Rounded asymmetric. Margin: Slightly undulated. Length (from base to tip): 36.0 mm to 38.0 mm. Width: 54.0 mm to 56.0 mm. Color (when fully opened): Upper surface: Basic color: Very light purple (RHS 76B). Over color: Slightly white (RHS NN155C) at the base; light reddish-purple shade (RHS N78D) and stripes (RHS N78B to N78C). Lower surface: Basic color: Very light purple (RHS 76C). Over color: Reddish-purple shade (RHS N78D) and stripes (RHS N78C).

*Dorsal sepal*.—Shape: Elliptic. Apex: Slightly emarginated. Margin: Entire. Length (from base to tip): 53.0 mm to 55.0 mm. Width: 35.0 mm to 37.0 mm. Color (when fully opened): Upper surface: Basic color: Light reddish-purple (RHS N78D). Over color: Slightly greenish-white (RHS 155C) at the base; purplish-pink stripes (RHS N78C) and very light purple margin (RHS 76D) toward the apex. Lower surface: Basic color: Light reddish-purple (RHS N78D). Over color: Slightly light yellow-green (RHS 145B) at the base; stripes (RHS N78C) and very light purple margin (RHS 76C) toward the apex.

*Lateral sepals*.—Shape: Ovate. Apex: Obtuse asymmetric. Margin: Entire. Length (from base to tip): 54.0 mm to 56.0 mm. Width: 33.0 mm to 35.0 mm. Color (when fully opened): Upper surface: Basic color: Very light purple (RHS 76B). Over color: Slightly yellow-green (RHS 145B) at the base; stripes (RHS N78D). Lower surface: Basic color:

Very light purple (RHS 76B). Over color: Slightly light green (RHS 146D) at the base; light reddish-purple (RHS N78D) and very light purple (RHS 76B) toward the tips.

*Labellum* (*lip*).—Whiskers: Present. Length of whiskers: 23.0 mm to 25.0 mm. Color of whiskers: Very light purple (RHS 76B) at the base with light greenish-yellow tips (RHS 8C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Undulated. Length: 23.0 mm to 25.0 mm. Width: 17.0 mm to 19.0 mm. Color: White (RHS NN155C) at the base with red stripes (RHS 185A); light yellow (RHS 160B) on one side; very light purple (RHS 76C) toward other margin.

*Apical lobe*.—Shape: Triangular. Margin: Entire. Length: 24.0 mm to 26.0 mm. Width: 25.0 mm to 27.0 mm. Color: Red (RHS 181A) and greenish-yellow (RHS 160C) at the base; very light purple (RHS 76B) toward whiskers.

*Callus*.—Average size: Large. Height: 6.0 mm to 7.0 mm. Length: 6.0 mm to 7.0 mm. Width: 5.0 mm to 6.0 mm. Color: Yellow (RHS 13A); dotted (RHS 185A).

Reproductive organs:

*Column*.—Length: 9.0 mm to 11.0 mm. Diameter: 5.3 mm to 5.8 mm. Color: Very light purple (RHS 76C) with light purple stripe (RHS 76A) in the middle.

*Pollinia*.—Quantity: 2. Diameter: 0.9 mm to 1.1 mm. Color: Orange-yellow (RHS 23A).

*Ovary*.—Length: 14.0 mm to 16.0 mm. Diameter: 2.6 mm to 2.9 mm. Color: Light yellow-green (RHS 145C) and very light purple (RHS 76C/D) toward the flower.

*Pedicel*.—Length: 42.0 mm to 44.0 mm. Diameter: 3.0 mm to 3.4 mm. Color: Purple (RHS N77A) at the base; light yellow-green (RHS 145B) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGORYQ' differs from female parent plant '01-2036' (unpatented) in that 'PHALGORYQ' has flowers with a basic color of very light purple and a shaded pattern, whiskers that are very light purple at the base with light greenish-yellow tips, and columns that are very light purple with a light purple stripe in the middle, whereas '01-2036' has flowers with a basic color of reddish-purple and an edged pattern, whiskers that are reddish-purple, and columns that are reddish-purple.

'PHALGORYQ' differs from male parent plant '01-1988' (unpatented) in that 'PHALGORYQ' has flowers with a basic color of very light purple and a shaded pattern, whiskers that are very light purple at the base with light greenish-yellow tips, and columns that are very light purple with a light purple stripe in the middle, whereas '01-1988' has flowers with a basic color of white and an even pattern, whiskers that are yellow, and columns that are white.

'PHALGORYQ' is most similar to the commercial *Phalaenopsis* plants named 'PHALAGUC' (unpatented) and 'PHALBOCIQ' (unpatented). 'PHALGORYQ' differs from the commercial variety 'PHALAGUC' in that 'PHALGORYQ' has a moderately elongated leaf base shape and rounded asymmetric petal apexes, whereas 'PHALAGUC' has a very elongated leaf base shape and emarginated petal apexes. Additionally, 'PHALGORYQ' has larger flowers than 'PHALAGUC'.

'PHALGORYQ' differs from the commercial variety 'PHALBOCIQ' in that 'PHALGORYQ' has rounded asymmetric petal apexes, whereas 'PHALBOCIQ' has obtuse petal apexes. Additionally, 'PHALGORYQ' has larger flowers and a larger plant height than 'PHALBOCIQ'.

I claim:

1. A new and distinct variety of *Phalaenopsis* plant named 'PHALGORYQ', substantially as described and illustrated herein.

* * * * *